United States Patent
Hakmiller

(10) Patent No.: US 9,914,898 B2
(45) Date of Patent: Mar. 13, 2018

(54) ENHANCED SEPARATION OF CORN OIL FROM THE ETHANOL MANUFACTURING PROCESS

(71) Applicant: Lincolnway Energy, LLC, Nevada, IA (US)

(72) Inventor: Eric Hakmiller, Ames, IA (US)

(73) Assignee: Lincolnway Energy, LLC, Nevada, IA (US)

( * ) Notice: Subject to any disclaimer, the term of this patent is extended or adjusted under 35 U.S.C. 154(b) by 0 days.

(21) Appl. No.: 15/063,023

(22) Filed: Mar. 7, 2016

(65) Prior Publication Data

US 2016/0257907 A1    Sep. 8, 2016

Related U.S. Application Data

(60) Provisional application No. 62/128,874, filed on Mar. 5, 2015.

(51) Int. Cl.
| | |
|---|---|
| *C11B 1/00* | (2006.01) |
| *C11B 1/12* | (2006.01) |
| *C11B 13/00* | (2006.01) |
| *C12P 7/06* | (2006.01) |

(52) U.S. Cl.
CPC ............ *C11B 1/12* (2013.01); *C11B 13/00* (2013.01); *C12P 7/06* (2013.01); *Y02E 50/16* (2013.01); *Y02W 30/74* (2015.05)

(58) Field of Classification Search
CPC ... C11B 13/00; C11B 1/10; C11B 3/00; C11B 3/001; C11B 1/00; C11B 1/02; C11B 1/025; C11B 1/04; C11B 1/08; C11B 3/003; C11B 3/006; C11B 3/10
USPC ........................................................ 554/8
See application file for complete search history.

(56) References Cited

U.S. PATENT DOCUMENTS 7,601,858 B2 * 10/2009 Cantrell ................ B01D 3/004
554/8

* cited by examiner

*Primary Examiner* — Deborah D Carr
(74) *Attorney, Agent, or Firm* — Nyemaster Goode, P.C.

(57) ABSTRACT

An ethanol production process and system for recovering high value oil products. The invention includes adding a heated lipid (oil) stream to a thin stillage stream to break the water/oil emulsion and free bound oil then recovering the oil. The process uses oil as the heat transfer mechanism to increase both the volume and quality of the oil recovered.

23 Claims, 4 Drawing Sheets

ENHANCED SEPARATION OF CORN OIL FROM THE ETHANOL MANUFACTURING PROCESS

BACKGROUND

A conventional dry grind milling process is shown in FIG. 1. As shown, the modern ethanol dry milled facility begins with a feedstock at step 10, such as field corn or sorghum, grinds that feedstock into flour with a hammer mill 12 then wets that flour to create a mash 14. Customarily, the mash is heated to about 180° F. and is cooled to about 90° F. prior to fermentation. The mash is customarily at a pH of between about 4.0 to 5.5. The mash 14 may be further ground in a fine grinding operation 16 or it may be transferred directly to a liquefaction tank 18 where enzymes are added to convert the starches in the mash to sugars 18. These sugars are thereafter converted into ethanol through fermentation 22. Following fermentation 22, the entire mix from the fermentation vessel is delivered to a distillation process 24 where it is further heated with the alcohol removed from the mix by vaporization which is recaptured by condensation thereby providing the primary product, ethanol 28, 30. Other purification steps, such as the use of molecular sieves 26, may also be employed in the process. The process mix remaining after the distillation step 24 is generally referred to as whole stillage.

The focus of the ethanol industry has traditionally been on the output of alcohol and maximization of production from the available starch for conversion. This conversion was accomplished in the front end of an ethanol plant, and once the alcohol was removed from the process stream, the plant was left with the task of disposing of large volumes of whole stillage. Traditionally, the "front end" of the process refers to the process steps which occur before fermentation and the "back end" refers to the process steps which occur after fermentation. In the early days of the modern ethanol production industry, this problem was simply addressed by removing water from the whole stillage and selling the remainder as a by-product for use as animal feed. This by-product was called distiller's dried grain (DDG) or distiller's dried grain with solubles (DDGS).

Beginning about the early 2000s, the industry began to also focus on the potential products presented by the whole stillage. As a result of sheer volume and water content, the industry focus was and remains on dewatering of whole stillage which, in the past, presented the opportunity to sell DDG or DDGS and, more recently, presents the opportunity to fraction the contents of the whole stillage to recover more useful by-products.

The dewatering process of the whole stillage follows distillation. The whole stillage is sent to a separation step 32. At the separation step 32, often involving the use of large horizontal centrifuges, the whole stillage is separated into a primarily heavy solids stream referred to as wet cake. The wet cake was historically sent to driers 36 for further dewatering in the production of DDGS.

The second stream emerging from the separation step 32 is a primarily liquid stream which contained mostly water with dissolved solubles and, also, a small percentage of solids. This liquid stream was referred to as the thin stillage steam. A portion of the liquid/thin stillage is recirculated back to the slurry mix 14 (stream labeled "back set" in the figures) so as to reduce the amount of fresh water introduced into the process and, further, to reduce the amount of thin stillage that required processing via the evaporators. Historically, the thin stillage is sent to the evaporation step 34 where it was subjected to a series of dewatering processes by circulation through multiple evaporators 34. One of the historic ethanol plant designs used a series of eight evaporators through which the thin stillage stream flowed, usually in series. In early ethanol plant designs, after completing the evaporation step 34, the resulting concentrated thin stillage stream was generally referred to as syrup, and the syrup was customarily added to the wet cake content in the drier 36 where further dewatering occurred in the production and recovery of DDGS 38. Optionally, if a nearby market existed, the syrup could be sold separately as a liquid animal feed supplement and, as it was not added to the wet cake in the drier 36, the resulting solid feed product that emerged from the driers was DDG. Also, with nearby markets, the wet cake could bypass the drier operation and be sold as wet DDG or the syrup could be sprayed upon the wet cake, with this mix bypassing the driers and sold as wet DDGS for use as animal feed.

In the 1950s, it was understood that the content of oil available from corn harvested in the United States was highly variable. In the article by Lofland, et. al., *Distribution of Fatty Acids in Corn Oil*, The Journal of the American Chemists Society, Vol. 31, 412-413 (October 1954), oil content in corn was found to vary from 1.13% to 13.80%. Also, when ethanol plants began operations in earnest, there was no ready market for corn oil and, further, there were no specifications utilized by plants that mandated the corn feedstock material contain a particular percentage of corn oil. This was in line with the industry focus on alcohol output and efficiencies of fermentation (i.e.—implementation of fine grind operations on the mash to expose more surface area of starch in the resultant mash which would undergo fermentation). As the focus in the industry was beginning to expand to include matters other than the efficiency and output of alcohol, the infant biodiesel industry began to move away from the use of soybean oil as its feedstock replacing it with corn oil. This emerging market propelled the ethanol industry to add well known processes of oil separation using centrifuges to their backside operations which processes were used to separate oil from the thin stillage stream. This oil separation process was most often implemented near the evaporators as it afforded the plant the opportunity to control the water content of the in-feed stream to the centrifuge so as to facilitate the mechanical separation of the corn oil. In operation, the thin stillage stream was frequently diverted from the piping connecting two of the evaporators; it was sent to centrifuges where it was processed with oil separating from the stream, and the thin stillage stream was thereafter returned to the piping system so as to flow into the evaporation unit where it was headed prior to diversion. As noted above, this stream would frequently thereafter be sent to the drier to become a part of the DDGS. The oil portion separated from the thin stillage stream was often further processed by storage in vessels that allowed the solids captured by centrifugation to separate with the remainder sold as corn oil.

One problem with traditional processes is that the thin stillage includes emulsions which capture and bind oil. The bound oil is difficult to separate from the thin stillage. Therefore, there is a need for a process which increases the amount of oil recovered from ethanol plants.

SUMMARY

One aspect of the invention includes an ethanol production process for recovering high value oil products. The process includes adding a heated stream of lipids (oils) to a thin stillage stream to break the water/oil emulsion in a way that does not damage the quality of the oil or add moisture to the system. The process uses oil as the heat transfer medium to increase both the volume and quality of the oil recovered.

One aspect of the invention includes an ethanol production process capable of recovering high value oil products wherein a stream of finished corn oil is drawn from the finished oil tank (i.e., it is recycled upstream) to create a lipid stream. The lipid stream is heated then reintroduced to the thin stillage stream to free bound oil and increase quality and quality of recovered oil. More specifically, the process includes taking a feedstock, wetting and grinding the feedstock to create a mash, then fermenting the mash to create a post-fermentation process stream having an alcohol. The post-fermentation process stream is separated to create an alcohol stream and a whole stillage stream. A thin stillage stream is separated from the whole stillage stream then oil is recovered from the thin stillage stream using centrifuges or other mechanical separators. The oil is heated and recycled back into the process (upstream) as a lipid stream which is introduced to the thin stillage stream. The heated lipid stream may be introduced to the thin stillage stream in a flash chamber, flash vented piping, or other apparatus known to the art, so that there is no resistance or disruption to the vaporization of the water and so as to facilitate maximized emulsion breaking within the thin stillage stream. The thin stillage lipid mixture is thereafter introduced to centrifuges or other mechanical separators where finished feedstock oil (such as corn oil) is separated and recovered. A portion of the recovered oil may (again) be recycled into the process (as described above) and a portion may be recovered for sale or further processing.

One aspect of the invention includes a system for recovering high value co-products from an ethanol process. The system includes grinding the feedstock into flour with a hammer mill, wetting the flour to create a mash in a slurry tank. Next, enzymes are added in a liquefaction tank to convert the starches in the feedstock mash to sugars. The stream exiting the liquefaction tank is sent to a fermentation tank where the sugars are converted into ethanol through fermentation. The whole stillage in the post-fermentation stream is separated in a separation unit to create an alcohol stream and a thin stillage stream. Oil is recovered from the thin stillage stream and stored in a finished oil tank. A lipid stream is taken from a finished oil tank and heated in a heat exchanger then introduced to the blending tank where it is mixed with the thin stillage stream to create a feedstock oil process stream. The feedstock oil process stream is introduced to mechanical separators which separate and recover a finished oil stream.

One aspect of the invention includes an ethanol production process capable of recovering high value oil products. The process includes taking a feedstock, wetting and grinding the feedstock to create a mash, then separating a lipid stream from the mash. The lipid stream is directed downstream to the back end of the process where it is heated and, thereafter, introduced into a thin stillage stream which has been recovered from an intermediate stage of the evaporation process or, depending upon moisture content of the syrup stream, recovered from the end of the evaporation process. The heated lipid stream may be introduced to the thin stillage stream in a flash chamber, flash vented piping, or other apparatus known to the art, so that there is no resistance or disruption to the vaporization of the water and so as to facilitate maximized emulsion breaking within the thin stillage stream. The thin stillage lipid mixture is thereafter introduced to centrifuges or other mechanical separators where finished feedstock oil (such as corn oil) is separated and recovered.

One aspect of the invention includes a process for recovering high value co-products from ethanol plants. The process includes grinding and wetting the feedstock to create a corn flow process stream comprising a fine grind mash; separating a lipid stream from the corn flow process stream; fermenting the corn flow process stream to create a post-fermentation process stream having an alcohol; separating the alcohol from the post-fermentation process stream leaving a whole stillage stream; separating a thin stillage stream from the whole stillage stream; heating the lipid stream; introducing the lipid stream to the thin stillage stream to create a corn oil process stream; and separating finished oil from the corn oil process stream.

One aspect of the invention includes a process for recovering high value co-products from ethanol plants. The process is similar to the ones described above, however, the lipid stream is directed to the thin stillage stream from a different point in the ethanol process or from an outside source that is separate from the ethanol process. In one embodiment the lipid stream is taken from an outside oil source and introduced to the thin stillage stream.

One aspect of the invention includes products produced by the processes described above.

One aspect of the invention includes a system for recovering high value co-products from an ethanol process. The system includes grinding the feedstock into flour with a hammer mill, wetting the flour to create a mash in a slurry tank, then further grinding the mash with a fine grinding mill. Next, enzymes are added in a liquefaction tank to convert the starches in the feedstock mash to sugars. The stream exiting the liquefaction tank is separated in a separation unit into a sugar stream and a lipid stream. The sugars are directed to a fermentation tank where they are converted into ethanol through fermentation. The whole stillage in the post-fermentation stream is separated in a separation unit to create an alcohol stream and a thin stillage stream which is directed to a blending tank. The lipid stream is heated in a heat exchanger then introduced to the blending tank where it is mixed with the thin stillage stream to create a feedstock oil process stream. The feedstock oil process stream is introduced to mechanical separators which separate and recover a finished oil stream.

BRIEF DESCRIPTION OF THE DRAWINGS

The advantages of the technology described may be better understood by referring to the descriptions below with the accompanying drawings. The drawings are not to scale and represent exemplary configurations that depict general principles of the technology which are not meant to limit the scope of the invention.

DETAILED DESCRIPTION

The processes of the present invention will now be described in detail by reference to various non-limiting embodiments, including the figures which are exemplary only.

Unless otherwise indicated, all numbers expressing dimensions, capacities, and so forth used in the specification and claims are to be understood as being modified in all instances by the term "about." Without limiting the application of the doctrine of equivalents to the scope of the claims, each numerical parameter should at least be construed in light of the number of reported significant digits and by applying ordinary rounding techniques.

The present invention may be practiced by implementing process steps in different orders than as specifically set forth herein. All references to a "step" may include multiple steps (or substeps) within the meaning of a step. Likewise, all references to "steps" in plural form may also be construed as a single process step or various combinations of steps.

The present invention may be practiced by implementing process units in different orders than as specifically set forth herein. All references to a "unit" may include multiple units (or subunits) within the meaning of a unit. Likewise, all references to "units" in plural form may also be construed as a single process unit or various combinations of units.

As used in this specification and the appended claims, the singular forms "a," "an," and "the" include plural referents unless the context clearly indicates otherwise.

Corn is used as an exemplary feedstock for the processes described herein. It should be noted, however, that other feedstocks such as sorghum may be used and the exemplary uses of the terms "corn flow", "corn oil", and other terms including the word "corn" should be read broad enough to include all suitable feedstocks.

One aspect of the invention includes a process for recovering high value co-products from an ethanol process. More specifically, the invention includes heating a lipid such as oil then introducing the heated lipid stream to a thin stillage stream to break emulsions and release bound oil from the thin stillage for recovery of the oil.

Figure 1:
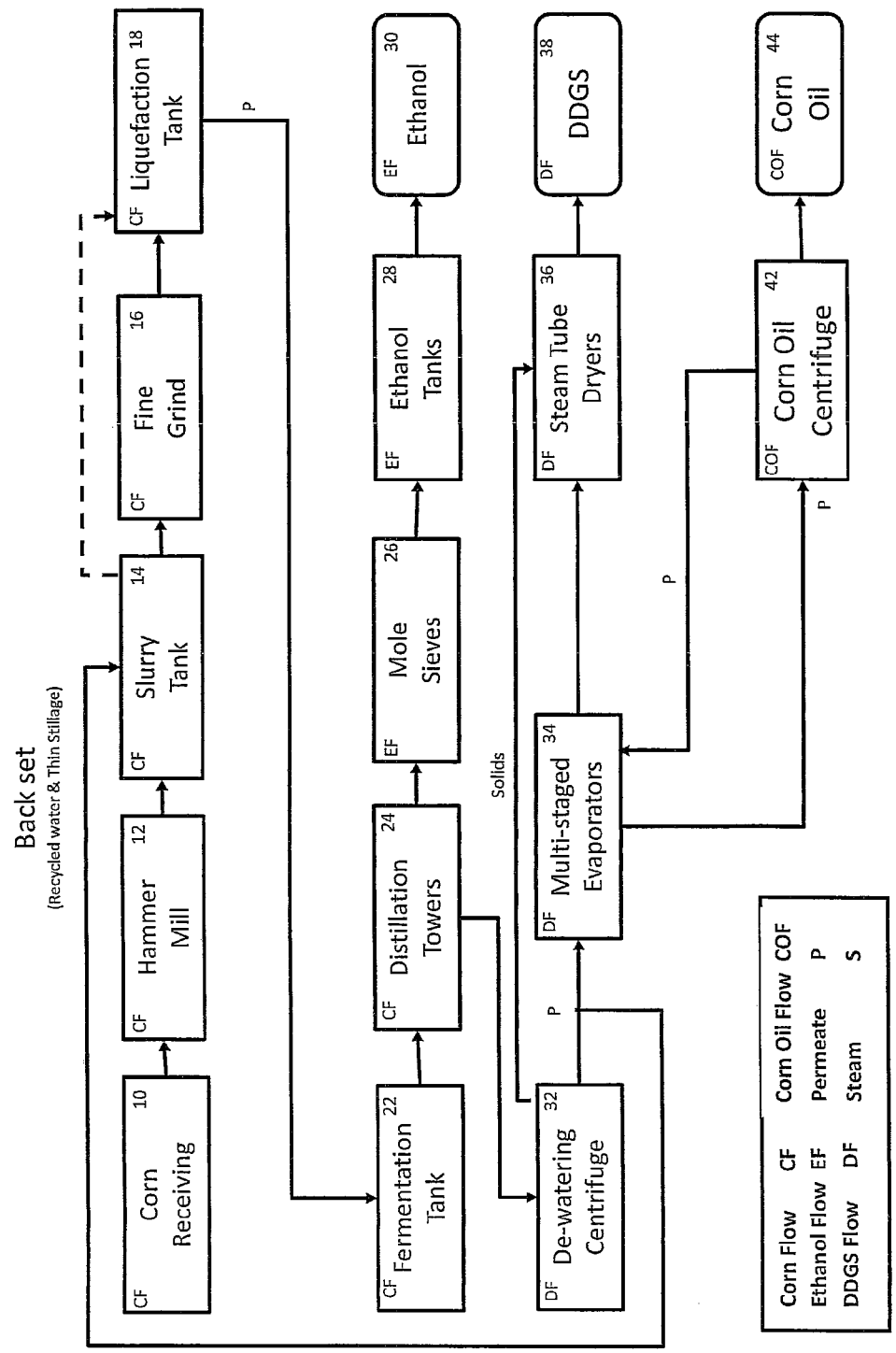
FIG. 1 is a flow chart showing an exemplary prior art ethanol production process.
Figure 2:
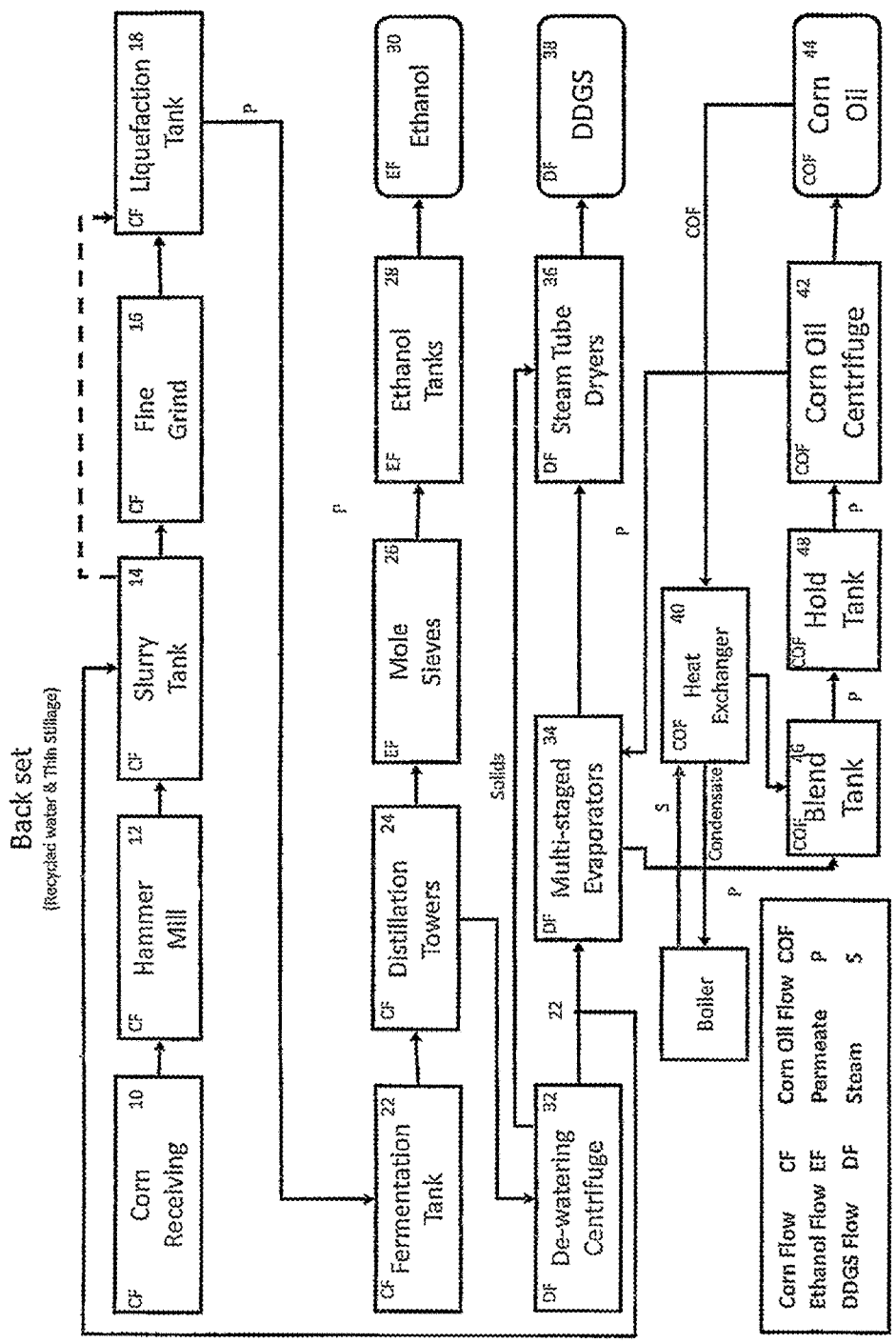
FIG. 2 is a flow chart showing an embodiment of the process where the lipid stream is taken from oil recovered from the ethanol process.

FIG. 2 shows one embodiment of the invention, which may include many of the traditional ethanol production steps discussed above and shown in FIG. 1. First, a feedstock such as corn or sorghum is introduced into a feedstock receiving vessel 10 to begin the feedstock flow stream (labeled "CF" in the figures). The feedstock is ground into flour with a hammer mill 12 then the flour is wet to create a mash 14. A fine grinding unit 16 may be used to further grind the mash which helps expose more surface area of the starch to enzymatic reactions and increases the yield. Other benefits associated with implementing the fine grinding operation in the front end of an ethanol process include the release of other useful components of the corn kernel including various lipids and other light density fractions. Next, enzymes are added in a liquefaction tank 18 to convert the starches in the corn mash to sugars 18. These sugars are thereafter converted into ethanol through fermentation 22.

Following fermentation 22, the product stream from the fermentation vessel 22 is delivered to a separation unit such as distillation units 24 where it is further heated with the alcohol removed from the fermentation product stream by vaporization, and is recaptured by condensation. As shown in FIG. 2, the distillation process 24 separates the corn flow stream into an ethanol flow stream (EF) comprising primarily alcohol and a DDGS flow stream (DF) comprising primarily fiber, protein, oil, and water. The ethanol flow stream is directed to further purification 26 and recovery 28, 30 processes, as is known in the art. The DDGS flow stream separated from the fermentation product stream is generally referred to as whole stillage. The whole stillage is sent to a separation unit such a de-watering centrifuge 32 where the whole stillage is separated into a primarily heavy solids stream referred to as wet cake, which may be directed to driers 36 for further dewatering in the production and recovery of DDGS 38.

The second stream separated from the whole stillage at separation step 32 is a primarily liquid stream which contains primarily dissolved solubles and, also, a small percentage of solids. This liquid stream is referred to as the thin stillage steam. The thin stillage may be sent to the evaporation step 34 where it is subjected to a series of dewatering processes by circulation through multiple evaporators 34. The thin stillage stream is then introduced to a heated lipid stream. As shown in FIG. 2, the lipid stream is introduced into the thin stillage stream at unit 46, which may be a blending tank (as shown) adapted to receive the two streams and allow them to mix. In an alternate embodiment the lipid stream is introduced into the pipe carrying the thin stillage (instead of into a blending tank) before introduction to the centrifuge 42. In this alternate embodiment the two streams mix within the pipes as the combined stream travels toward the next process unit.

In one embodiment, the lipid stream includes about between 98-100% oil. In another embodiment the lipids stream includes more than about 80% oil with the rest being primarily a mix of gums and other phosphatides. In another embodiment the lipid stream includes between about 70% and 90% lipids (oil) with the rest being primarily a mix of gums and other phosphatides. The pH may be between about 4.0 and about 5.5, with a preferred range tending more acidic—about 4.0 to 5.2. This chemical construct of the lipid stream (i.e., its high oil content) allows it to remain very stable under high heat conditions. This allows the heated lipid to facilitate the breaking of emulsions latter in the process (as described below). In order to effectively heat the lipid stream, however, it is preferred that its moisture content be not more than about 5%. Various additives are known and available that could be introduced into the lipid stream to increase stability when heated.

In one embodiment, the lipid stream is heated at step 40 before it is introduced to the thin stillage stream at 46. The lipid stream is heated at step 40 to between about one hundred ninety (190) degrees F. to three hundred twenty-five (325) degrees F. In one embodiment the lipid stream is heated at step 40 to about between two hundred and five (205) degrees F. and two hundred and fifteen (215) degrees F. The heating step 40 can be done using any suitable device, including a plate and frame heat exchanger or in a tube and shell heat exchanger. The heating step 40 may include one or more separate heating steps or heat exchangers. After heating, the lipid stream is introduced into the process stream at step 46 (which is now primarily a thin stillage stream that has been separated from the whole stillage).

In one embodiment the thin stillage stream has a larger flow volume than the lipid stream which helps prevent degradation, which may otherwise occur if the thin stillage was subject to a continuous and prolonged temperature increase. The larger flow volume of the thin stillage stream allows it to experience a fleeting but sharp rise in temperature at the point of contact 46 with the lipid stream. As a result of process operations resulting in the agitation and churning of the process stream, pH, and the presence of small, insoluble solids in the process stream, a portion of the corn oil in the thin stillage is bound in an oil-in-water (O/W) emulsion which operates to impede the mechanical separation of the oil from the stream. The addition of the hot lipid stream to the thin stillage at step 46 results in a dynamic energy imbalance in the O/W emulsion which causes the water of the emulsion to vaporize or flash off. This operation frees the bound oil 44 in the thin stillage which is available to be removed in the back end centrifuges or other mechanical separators 42. The hot lipid also decreases the viscosity of the total flow and weakens any emulsion so that more thin stillage can be processed through the backend mechanical separators 42 to recover more oil 44.

In one embodiment, the corn oil flow (COF) stream exiting the blend tank 46 is directed to a holding tank 48 to allow for gravity separation before the stream is further directed to a mechanical separator 42 such as a centrifuge. The mechanical separator 42 separates the corn oil flow stream into a finished oil product stream and a thin stillage stream. The thin stillage stream is thereafter directed into evaporation 34 or drying 36 units where it is eventually recovered as DDGS 38. The finished oil product stream is recovered at step 44 and stored in an oil storage tank or directed to further purification processes.

In one embodiment shown in FIG. 2, the lipid stream is taken from the storage tank 44 holding the finished oil product which has already been recovered from thin stillage in the ethanol process. This oil can be safely heated up to the desired temperature as it is free of the solubles present in thin stillage. It is introduced to the thin stillage stream at step 46 in order to free bound oil and break the resident emulsion in that stream (as described above) for downstream recovery of the oil. In this embodiment, the lipid stream is taken from the back end of the process (finished oil tank 44) and recycled upstream to another part of the back end of the process.

Figure 3:
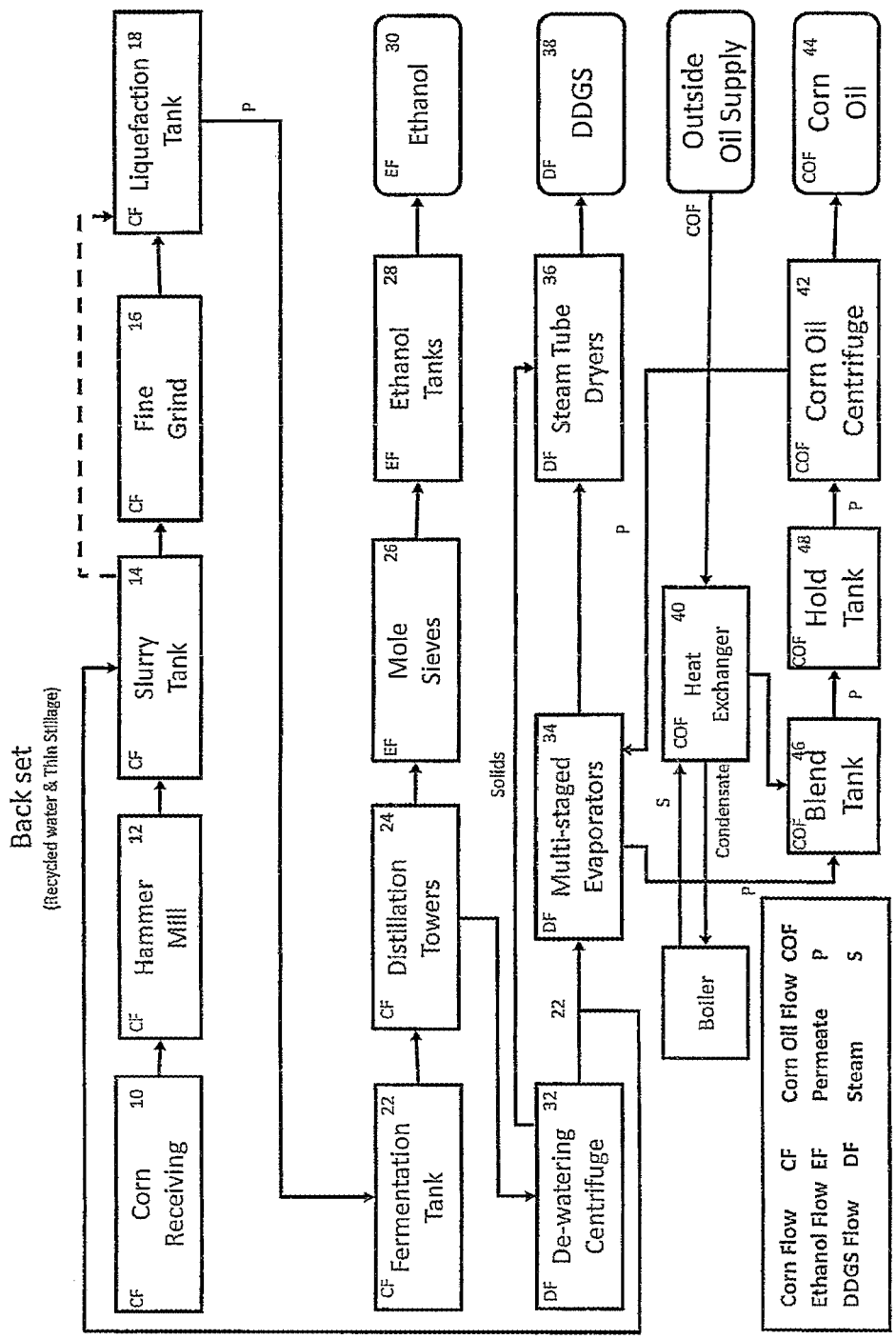
FIG. 3 is a flow chart showing an embodiment of the process where the lipid stream is taken from an outside oil source.

Alternate embodiments include alternate sources of the lipid stream. FIG. 3 shows an alternate embodiment wherein the lipid stream is taken from an outside source (i.e., a source unrelated to the ethanol production process). As described above, the lipid stream is introduced to the thin stillage stream at step 46 in order to free bound oil and break the resident emulsion in that stream for downstream recovery of the oil.

Figure 4:
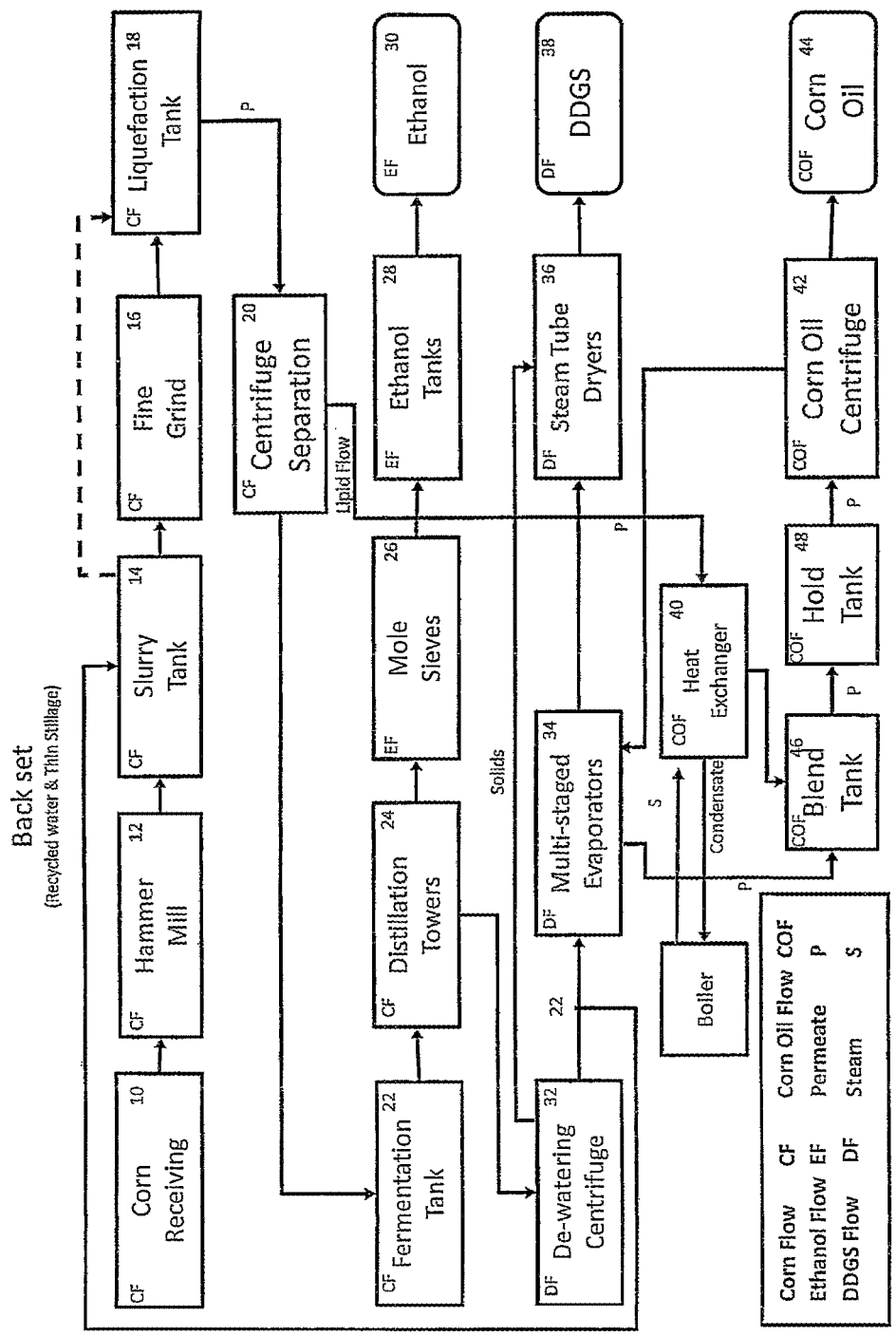
FIG. 4 is a flow chart showing an embodiment of the process where the lipid stream is recovered from the front end of the process then introduced to the thin stillage stream at the back end of the process.

In an alternate embodiment shown in FIG. 4, the lipids and other light density fractions are separated from the mash (referred to in FIG. 4 as the corn flow stream) at separation unit 20 prior to fermentation to form the lipid stream and a mash stream. The mash stream is directed to the fermentation tank 22 as described above. Separation step 20 removes one or more nonfermentable components (i.e., oil) from the corn flow stream which, in turn, results in the increase of alcohol yield per volume within the fermentation vessel 22. Additional benefits to the removal of the lipid stream from the mash/corn flow stream include the reduction or elimination of downstream fouling of equipment, particularly within the evaporation units 34 wherein deposits of the lipid material within the piping system requiring shutdown and cleaning operations on a periodic basis. After separation from the mash/corn flow stream, the lipid stream is directed downstream where it is reintroduced into the process stream at step 46 as shown in FIG. 2. In this embodiment, the lipid stream is taken from the front end of the ethanol production process and reintroduced to the back end of the process.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is as follows:

1. A process for the recovery of oil from an ethanol process comprising:
   processing a feedstock to create a process stream;
   fermenting the process stream to create a post-fermentation process stream;
   separating the post-fermentation process stream into an alcohol stream and a whole stillage stream;
   separating a thin stillage stream from the whole stillage stream, wherein the thin stillage stream includes bound oil;
   introducing a heated lipid stream to the thin stillage stream to create an oil flow stream;
   separating an oil product from the oil flow stream.

2. The process of claim 1 further comprising the step of storing the oil product in an oil storage tank.

3. The process of claim 2 wherein the lipid stream is taken from the oil storage tank.

4. The process of claim 1 wherein lipids are recovered from a point in the ethanol process to create the lipid stream.

5. The process of claim 1 wherein the lipid stream is separated from the process stream prior to fermentation.

6. The process of claim 1 wherein the lipid stream is heated in a heat exchanger prior to being introduced to the thin stillage stream.

7. The process of claim 1 wherein the lipid stream is heated to a temperature of between about 190 degrees F. and 325 degrees F. before being introduced to the thin stillage stream.

8. The process of claim 1 wherein the lipid stream is heated to a temperature of between about 205 degrees F. and 215 degrees F. before being introduced to the thin stillage stream.

9. The process of claim 1 wherein the thin stillage stream is separated from the whole stillage stream using a centrifuge.

10. The process of claim 1 wherein the oil product is separated from the oil flow stream using a centrifuge.

11. The process of claim 1 wherein upon introducing the heated lipid stream to the thin stillage stream, the heated lipid stream breaks emulsions in the thin stillage releasing bound oil.

12. The process of claim 1 wherein upon introducing the heated lipid stream to the thin stillage stream, the heated lipid stream decreases the viscosity of the thin stillage.

13. The process of claim 1 wherein upon introducing the heated lipid stream to the thin stillage stream, the heated lipid stream vaporizes water from the thin stillage.

14. The process of claim 1 wherein the lipid stream comprises at least 80% oil.

15. A process for the recovery of oil from an ethanol process comprising:
   processing a feedstock to create a process stream;
   fermenting the process stream to create a post-fermentation process stream;
   separating the post-fermentation process stream into an alcohol stream and a whole stillage stream;
   separating a thin stillage stream from the whole stillage stream, wherein the thin stillage stream includes bound oil;

separating an oil stream from the thin stillage stream to create a lipid stream;
heating the lipid stream and recycling it to the thin stillage stream;
recovering an oil product.

16. The process of claim 15 wherein the lipid stream is heated to a temperature of between about 205 degrees F. and 215 degrees F. to create the heated lipid stream before being introduced to the thin stillage stream.

17. The process of claim 15 wherein the thin stillage stream is separated from the whole stillage stream using a centrifuge.

18. The process of claim 15 wherein upon introducing the heated lipid stream to the thin stillage stream, the heated lipid stream breaks emulsions in the thin stillage releasing bound oil.

19. A process for the recovery of oil from an ethanol process, said process comprising:
grinding and wetting a feedstock to create a process stream;
separating a lipid stream from the process stream;
fermenting the process stream to create a post-fermentation process stream having an alcohol;
separating the post-fermentation process stream into an alcohol stream and a whole stillage stream;
separating a thin stillage stream from the whole stillage stream, wherein the thin stillage stream includes bound oil;
heating the lipid stream to produce a heated lipid stream; and
introducing the heated lipid stream to the thin stillage stream to create an oil flow stream;
separating an oil product from the oil flow stream;
wherein the lipid stream is separated from the process stream before fermentation.

20. The process of claim 19 wherein the lipid stream is heated to a temperature of between about 205 degrees F. and 215 degrees F. to create the heated lipid stream before being introduced to the thin stillage stream.

21. The process of claim 19 wherein the thin stillage stream is separated from the whole stillage stream using centrifuge.

22. The process of claim 19 wherein the oil product is separated from the oil flow stream using a centrifuge.

23. The process of claim 19 wherein upon introducing the heated lipid stream to the thin stillage stream, the heated lipid stream breaks emulsions in the thin stillage releasing bound oil.

* * * * *